Figure 1:
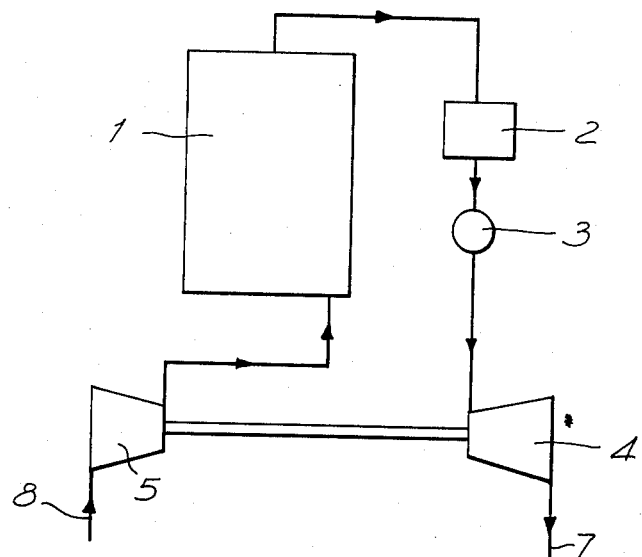

United States Patent [19]

Maslen et al.

[11] 4,237,693

[45] Dec. 9, 1980

[54] ENERGY RECOVERY SYSTEM

[75] Inventors: Frank P. Maslen; Geoffrey B. Cordell, both of Stockton-on-Tees, England

[73] Assignee: Imperial Chemical Industries Limited, London, England

[21] Appl. No.: 931,156

[22] Filed: Aug. 4, 1978

[30] Foreign Application Priority Data

Aug. 9, 1977 [GB] United Kingdom ............... 33338/77

[51] Int. Cl.³ ............................. F02C 1/04; F02C 7/02
[52] U.S. Cl. ......................................... 60/648; 60/645; 60/650
[58] Field of Search ................... 48/197 A; 210/12, 2, 210/15, 63 R, 180; 435/813; 60/648, 650, 682, 721, 643, 645; 71/9; 422/187

[56] References Cited

U.S. PATENT DOCUMENTS

| 3,905,197 | 9/1975 | Miller | 60/649 X |
| 3,928,973 | 12/1975 | Hand | 60/648 |

Primary Examiner—Allen M. Ostrager
Attorney, Agent, or Firm—Cushman, Darby & Cushman

[57] ABSTRACT

An energy recovery system for use in conjunction with a fermenter operating with an overpressure preferably of 5 to 10 bars gauge. Gas under pressure leaving the fermenter passes to a gas expander and the power produced by the expander is used to drive the compressor which supplies gas under pressure to the fermenter. The combination of the energy recovery system with a fermenter provides an efficient means for operating a process for the production of single cell protein.

10 Claims, 2 Drawing Figures

ENERGY RECOVERY SYSTEM

This invention relates to an energy recovery system for use in combination with a fermentation process of the kind in which a feed gas, having passed through a compressor, is supplied under pressure to the process and an off-gas under pressure is released from the process. More particularly the process of the kind described is an aerobic fermentation process, the feed gas being an oxygen-containing gas such as air and the off-gas comprising the feed gas depleted in oxygen together with carbon dioxide produced in the process.

Large scale aerobic fermentation processes such as processes for the production of single cell protein, require large amounts of energy and in the commercial operation of such processes the efficient use of energy is important.

According to the present invention we provide a fermentation process of the kind described wherein the off-gas at above atmospheric pressure is passed to an energy recovery system in which it is heated and thereafter expanded in a gas expander and the resulting power produced by the gas expander is transmitted to the compressor and supplies all or part of the power requirements thereof in compressing the feed gas.

Further according to the invention we provide an apparatus comprising a fermenter for the operation of a fermentation process of the kind described together with an energy recovery system wherein the energy recovery system comprises a gas expander which provides all or part of the power requirements of the compressor or compressors in compressing the feed gas, gas conducting means for conducting the off-gas to the expander, heating means for heating the off-gas before it enters the expander and power transmitting means for transmitting power from the expander to the compressor.

Preferably in the process and apparatus of the invention the gas expander can supply power in excess of that required by the compressor(s), thus allowing an export of power for other uses.

The invention will be described hereinafter in terms of its application in an aerobic fermentation process.

Suitably the process is a process for the production of single cell protein for example a process in which a methanol-utilising bacterium is cultured in a methanol-containing medium. The apparatus is suitably a fermenter such as those described in our UK specification Nos. 1353008, 1417486 and 1417487 and in our co-pending UK application No. 52430/74 (U.S. application Ser. No. 931,725, filed Aug. 7, 1978), having a riser and a downcomer which communicate with each other. Such fermenters have not hitherto been operated at a significant overpressure in order to avoid the harmful effects believed to be caused by undue concentrations of dissolved carbon dioxide on microorganisms in a culture. However we have now found that microorganisms of the species *Methylophilus methylotrophus* (formerly *Pseudomonas methylotropha*), described in our UK specification No. 1370892, have a tolerance to carbon dioxide which is such that significant overpressures can be used. When such fermenters are operated with an overpressure they can be used in connection with the present invention. In this case they are operated in such a manner that there is a gas pressure of at least 2 bars gauge in the space above that occupied by a culture in the fermenter.

We have found that as the pressure above the culture is increased the energy which can be recovered using the expander rises more rapidly than the energy required by the compressor(s), i.e. the net power requirement falls and additionally the operation of the fermenter is improved. Therefore off-gas suitably leaves the fermenter at a pressure of at least 2 bars gauge, preferably between 2 and 15 bars gauge. Most suitably the pressure of the off-gas is between 3 and 10 bars gauge.

On leaving the fermenter the off-gas will typically be at a temperature of approximately 40° C.

If this gas is supplied directly to a gas expander then the work energy available is substantially less than the energy required by the compressor. Also, the vapour present in the gas is likely to condense causing damage to the expander. Thus the off-gas is preferably heated to a temperature limited at the lower value by the need to prevent condensation in the expander and at the upper value by the suitability of the expander. For preferred operation the two extremes are thus:

(A) To heat the gas to a temperature as high as possible consistent with a reliable expander. In this case it is likely that the expander will provide the power required by the process air compressor or compressors and additionally supply power for other purposes, i.e. "export" power.

(B) To heat the gas to a temperature which is sufficiently high to avoid harmful condensation in the expander, i.e. the gas is heated to a temperature such that at no time whilst it is in the expander does its temperature fall below the dew point. In this case the expander will probably only provide part of the power necessary to drive the process air compressor or compressors.

Figure 3:
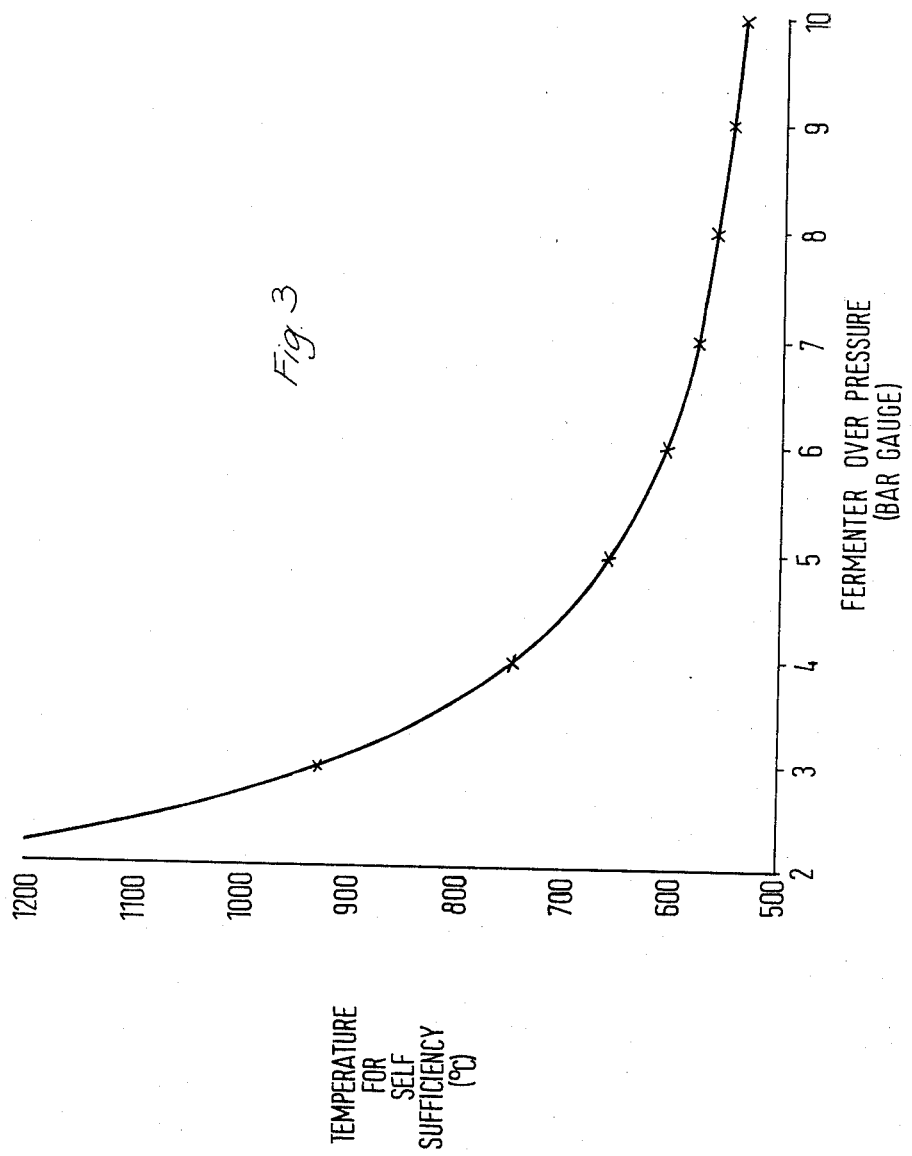

Provided the overpressure is sufficient it is found that there is a particularly advantageous case between these two extremes at which the available energy from the expander is just sufficient to supply all the energy for the compressor i.e. self sufficiency. Typical combinations of temperature and the expander inlet pressure required to achieve self sufficiency are shown in FIG. 3 which is constructed for a 60 meter high fermenter operating under a pressure of 6 bar gauge. Points above and to the right of the curve show that excess energy is available and it is therefore possible to supply power for other purposes i.e. export power. Points below and to the left indicate that some additional power is required.

The temperature required for self sufficiency is a strong function of expander inlet pressure. Specifically the practical temperature limitations imposes the need to use substantial expander inlet pressures.

In (A) the gas is suitably preheated to a temperature within the range 400° C. to 1200° C. before entering the expander, for example to 650° C. In (B) the pre-heating temperature is suitably in the range 100° to 400° C. for example 260° C.

The gas leaving the fermenter may contain liquid/solid matter carried over from the culture which could impair the effectiveness of the expander. To minimise the amount of liquid/solid matter in the gas entering the expander a suitable separation device may be included in the system between the fermenter and the expander.

Before entering the expander the gas may be preheated by any suitable method. Suitable methods include:

(i) A heat exchanger using the gas expander or compressor exhaust. This method may be combined with either of methods (ii) or (iii) below.

(ii) Adding hot flue gas, from a separate heat generator, to the gas from the fermenter.

(iii) Burning a fuel in the gas from the fermenter. This is possible since the gas leaving the fermenter will contain sufficient oxygen. In addition this apparatus may be designed to incinerate any combustible material in the off-gas. The apparatus may also include means for removing harmful chemicals such as sulphur oxides which could damage the expander. This may be done in the combustion apparatus or at a later stage in the system.

From the gas expander the fermenter off-gas, (which normally will be at a pressure of about 1 bar absolute,) may be discharged into the atmosphere. However this gas may be at a high temperature and it can be used to provide heat for other stages of an overall fermentation process. In the production of single cell protein for example it may be used to generate steam for feed sterilisation or other process duties or to provide heat for drying the protein product directly or indirectly using a gas/air heat exchanger. The gas is particularly suitable for the direct drying of the protein product as the oxygen content has been reduced well below the value at which mixtures containing protein dust can give rise to explosions.

The advantage of the energy recovery system of the invention is that it makes use of the super atmospheric pressure of the fermentation process off-gas to enable cheap heat energy to be used efficiently to provide some or all of the work energy required to drive the process gas compressor.

The invention is illustrated by the accompanying drawings wherein

Figure 2:
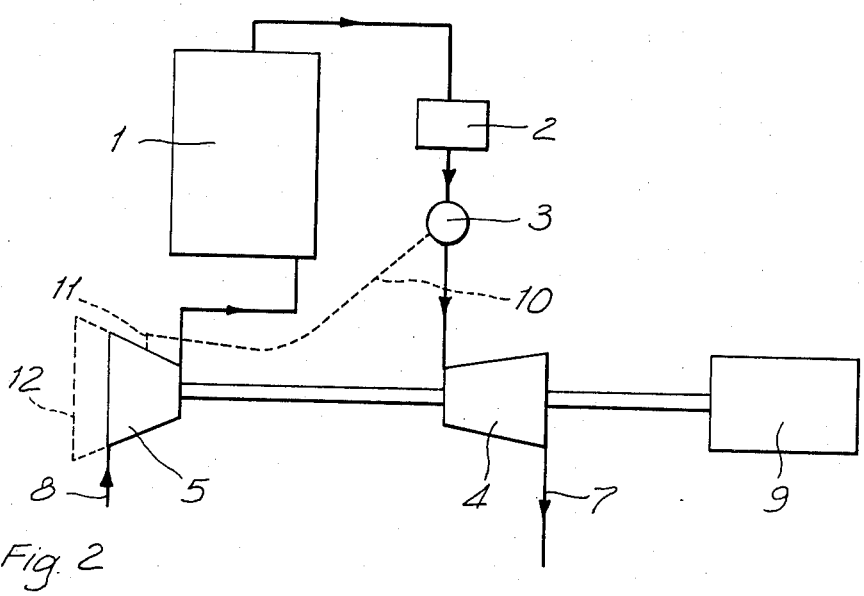

FIGS. 1 and 2 are schematic diagrams of two energy recovery systems according to the invention used in conjunction with fermenters.

FIG. 1 shows energy recovery system alternative (1) which is a self-sufficient system. Off-gas leaving a fermenter 1 through withdrawal means (line between fermenter 1 and separator 2) passes as shown via separator 2 and pre-heater 3 to expander 4 from whence it is exhausted along line 7. Air entering fermenter 1 passes as shown along line 8 and is compressed by compressor 5. All the power for compressor 5 is supplied by expander 4.

FIG. 2 can be used to illustrate energy recovery system alternatives (2) and (3). Regarding their basic components these are the same as alternative (1), the essential differences being as follows:

In alternative (2), the power supplied by expander 4 is insufficient to drive of itself compressor 5 and an auxiliary power source is required. This is shown as 9.

In alternative (3), the power supplied by expander 4 is in excess of that required by compressor 5. There is an export of power which can be supplied to an alternator. In this alternative therefore 9 is an alternator.

A useful refinement is shown in broken lines in FIG. 2. In this air is supplied from point 11 of compressor 5, which is enlarged as shown by 12, along line 10 to pre-heater 3. This gives the system a degree of flexibility in operation for the following reasons:

(a) It becomes possible to adjust the temperature in expander 4 either by directly cooling air leaving the pre-heater or by enabling more gas to be burnt in the pre-heater thus raising the temperature of the air.

(b) It enables more gas to be burnt in the pre-heater giving a temperature increase, in a situation in which there is insufficient oxygen in the gas leaving the fermenter.

When this refinement is included it is necessary to have a larger compressor. Line 10 takes gas from a position 11 which is part-way along the compressor since the gas pressure required is that of the fermenter exit gas rather than of the inlet gas. As an alternative to an enlarged compressor, two compressors could be used, air line 10 leading off from the first of these. The refinement could also, although less conveniently, be effected using gas from a source other than compressor 5.

The operation of alternatives (1) to (3) is illustrated in the following examples.

EXAMPLE 1

Consider the energy recovery system shown in FIG. 1. With a fermenter 60 m high and with an expander limited to 660° C., it is necessary to operate with a fermenter overpressure of 5 bar gauge in order to achieve self sufficiency. For larger overpressures, self sufficiency can be achieved with expander inlet temperatures lower than 660° C. (see FIG. 3) but there is an upper limit on overpressure determined by consideration of $CO_2$ toxicity on the microorganism. With the fermenter 1 operating with an overpressure of 5 bar gauge with the compressor 5 delivering 90 kg/sec air, the compressor requires approximately 27 MW power. Off-gas leaves the fermenter at a rate of 85 kg/sec and at a temperature of 40° C. Natural gas is burnt in pre-heater 3 at a rate of 1.1 kg/sec to raise the temperature of the off-gas from 40° C. to 660° C. The power recovered in expander 4 is 27 MW which is just sufficient to drive the compressor. The expander exhaust which is a temperature of 430° C. is passed along line 7 to another heating system and produces an energy saving of 0.5 kg/sec of natural gas or the equivalent thereof of another fuel being used there.

EXAMPLE 2

For the alternative (2) energy recovery system shown in FIG. 2, consider a fermenter 60 meters high and operating with an overpressure of 6 bar gauge. If the compressor is delivering 90 kg/sec air, the power required is 28 MW. Off-gas leaves the fermenter at a rate of 85 kg/sec and at a temperature of 40° C. Natural gas is burnt in preheater 3 at a rate of 0.4 kg/sec to raise the temperature of the off-gas from 40° C. to 260° C. The power recovered in the expander 4 is 16 MW. Thus, whilst an additional power source providing 12 MW is required, 16 MW of the necessary power is being generated by an extremely efficient method.

EXAMPLE 3

For the energy recovery system, alternative (3), shown in FIG. 2 consider a fermenter 60 meters high and operating at a pressure of 5 bar gauge. If the compressor is delivering 90 kg/sec air, the power required is 27 MW. Off-gas leaves the fermenter at a rate of 85 kg/sec and at a temperature of 40° C. Natural gas is burnt in pre-heater 3 at a rate of 1.2 kg/sec to raise the temperature of the off-gas to 725° C. The power recovered in expander 4 is 27.8 MW. Thus there is an export of 0.8 MW of power to alternator 9.

In the above examples 1 to 3 smplified systems have been considered to illustrate the efficacy of the invention clearly. The effect of introducing the refinement shown in broken lines on FIG. 2 has been ignored.

We claim:

1. An aerobic fermentation process utilizing a compressor, a fermenter, and a gas expander, comprising the steps of
    feeding an oxygen containing gas to the compressor;
    compressing the oxygen containing gas in the compressor to provide a feed gas having a pressure of at least about 2 bars gauge;
    feeding the feed gas into the fermenter to provide an overpressure in the fermenter of at least about 2 bars gauge;
    withdrawing off-gas from the fermenter, the withdrawn gas having a pressure of at least about 2 bars gauge;
    heating the withdrawn off-gas to a temperature high enough to prevent condensation in the gas expander;
    feeding the heated off-gas to the gas expander to produce power; and
    transmitting the resulting power from the gas expander to the compressor to supply all or part of the power requirements thereof in compressing the feed gas.

2. A process according to claim 1 wherein the power produced by the gas expander exceeds the power requirements of the compressor, the excess being used for another purpose.

3. A process according to claim 1 wherein off-gas leaves the fermenter at a pressure between 3 and 10 bars gauge.

4. A process according to claim 1 wherein off-gas is heated to a temperature within the range 400° to 1200° C. before entering the expander.

5. A process according to claim 1 wherein off-gas is heated to a temperature within the range 100° to 400° C. before entering the expander.

6. Apparatus for effecting aerobic fermentation, comprising
    a fermenter;
    compressor means for compressing oxygen-containing gas to a pressure sufficient to provide an overpressure of at least about 2 bars guage in the fermenter;
    a line for feeding oxygen-containing gas to the compressor means;
    a line for leading compressed oxygen-containing gas from the compressor means to the fermenter;
    withdrawal means for withdrawing off-gas from the fermenter having a pressure of at least about 2 bars gauge;
    a gas expander;
    means for heating the withdrawn off-gas to a temperature high enough to prevent condensation in the gas expander;
    means for feeding off-gas from the heating means to the gas expander to produce power; and
    means for transmitting the resulting power from the gas expander to the compressor means to supply all or part of the power requirements thereof in compressing feed gas.

7. An apparatus according to claim 6 wherein in addition to the power transmitting means from the expander to the compressor means there is a further power transmitting means for transmitting power to or from the expander.

8. An apparatus according to claim 6 wherein means for separing liquid or solid matter from the gas stream is positioned between the fermenter and the expander.

9. An apparatus according to claim 6 wherein means is provided for supplying gas from the compressor means to the heating means.

10. An apparatus according to claim 6 wherein means is provided for transmitting gas from the expander to another system.

* * * * *